(12) United States Patent
Talpade et al.

(10) Patent No.: US 9,042,965 B2
(45) Date of Patent: *May 26, 2015

(54) BIOPSY MARKER WITH IN SITU-GENERATED IMAGING PROPERTIES

(71) Applicant: C. R. Bard, Inc., Tempe, AZ (US)

(72) Inventors: Dnyanesh A. Talpade, Kinnelon, NJ (US); Chandrashekhar Pathak, Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 222 days.

This patent is subject to a terminal disclaimer.

(21) Appl. No.: 13/787,331

(22) Filed: Mar. 6, 2013

(65) Prior Publication Data

US 2013/0184562 A1    Jul. 18, 2013

Related U.S. Application Data

(63) Continuation of application No. 12/519,656, filed as application No. PCT/US2007/087768 on Dec. 17, 2007, now Pat. No. 8,401,622.

(60) Provisional application No. 60/870,502, filed on Dec. 18, 2006.

(51) Int. Cl.
*A61B 5/06* (2006.01)
*A61B 6/12* (2006.01)
(Continued)

(52) U.S. Cl.
CPC ................. *A61B 5/064* (2013.01); *A61B 19/54* (2013.01); *A61K 49/0002* (2013.01); *A61K 49/0409* (2013.01); *A61K 49/18* (2013.01); *A61K 49/222* (2013.01); *A61B 5/055* (2013.01); *A61B 5/062* (2013.01); *A61B 6/12* (2013.01); *A61B 8/0833* (2013.01); *A61B 10/02* (2013.01); *A61B 2019/5466* (2013.01); *A61B 2019/5408* (2013.01); *A61B 2019/5425* (2013.01);
(Continued)

(58) Field of Classification Search
USPC .................. 600/424, 431, 414, 426; 424/423
See application file for complete search history.

(56) References Cited

U.S. PATENT DOCUMENTS 2,481,408 A    9/1949 Fuller et al.
2,899,362 A    8/1959 Sieger, Jr. et al.
(Continued)

FOREIGN PATENT DOCUMENTS

DE    1029528 B    5/1958
EP    0146699 A1    7/1985
(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages, 1998.
(Continued)

*Primary Examiner* — Long V Le
*Assistant Examiner* — Farshad Negarestan (57) ABSTRACT

An intracorporeal marker, for marking a site within living tissue of a host, includes an outer body portion of biodegradable material. An inner body portion is located in the outer body portion. The inner body portion includes biological material that becomes calcified in the living tissue of the host over time. An agent interacts with the biological material to promote calcification of the biological material of the inner body portion in the living tissue of the host.

16 Claims, 1 Drawing Sheet

(51) Int. Cl.
  *A61B 10/02* (2006.01)
  *A61B 5/055* (2006.01)
  *A61B 19/00* (2006.01)
  *A61K 49/00* (2006.01)
  *A61K 49/04* (2006.01)
  *A61K 49/18* (2006.01)
  *A61K 49/22* (2006.01)
  *A61B 8/08* (2006.01)

(52) U.S. Cl.
  CPC . *A61B2019/5495* (2013.01); *A61F 2250/0098* (2013.01)

(56) References Cited

U.S. PATENT DOCUMENTS

| | | |
|---|---|---|
| 2,907,327 A | 10/1959 | White |
| 3,005,457 A | 10/1961 | Millman |
| 3,128,744 A | 4/1964 | Jefferts et al. |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,820,545 A | 6/1974 | Jefferts |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,312,435 A | 5/1994 | Nash et al. |
| 5,320,100 A | 6/1994 | Herweck et al. |
| 5,320,613 A | 6/1994 | Houge et al. |
| 5,328,955 A | 7/1994 | Rhee et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |

(56) References Cited

U.S. PATENT DOCUMENTS

| | | |
|---|---|---|
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,716,981 A | 2/1998 | Hunter et al. |
| 5,747,060 A | 5/1998 | Sackler et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |

(56) References Cited

U.S. PATENT DOCUMENTS

| | | |
|---|---|---|
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,629,947 B1 | 10/2003 | Sahatjian et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,041,047 B2 | 5/2006 | Gellman et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,135,978 B2 | 11/2006 | Gisselberg et al. |
| 7,160,258 B2 | 1/2007 | Imran et al. |
| 7,172,549 B2 | 2/2007 | Slater et al. |
| 7,189,206 B2 | 3/2007 | Quick et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,280,865 B2 | 10/2007 | Adler |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,407,054 B2 | 8/2008 | Seiler et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,670,350 B2 | 3/2010 | Selis |
| 7,783,336 B2 | 8/2010 | Macfarlane et al. |
| 7,819,819 B2 | 10/2010 | Quick et al. |
| 7,844,319 B2 | 11/2010 | Susil et al. |
| 7,877,133 B2 | 1/2011 | Burbank et al. |
| 7,914,553 B2 | 3/2011 | Ferree |
| 7,945,307 B2 | 5/2011 | Lubock et al. |
| 7,983,734 B2 | 7/2011 | Jones et al. |
| 8,011,508 B2 | 9/2011 | Seiler et al. |
| 8,052,658 B2 | 11/2011 | Field |
| 8,064,987 B2 | 11/2011 | Carr, Jr. |
| 8,128,641 B2 | 3/2012 | Wardle |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,320,995 B2 | 11/2012 | Schwamb, Jr. |
| 8,334,424 B2 | 12/2012 | Szypka |
| 8,361,082 B2 | 1/2013 | Jones et al. |
| 8,437,834 B2 | 5/2013 | Carr, Jr. |
| 8,454,629 B2 | 6/2013 | Selis |
| 8,486,028 B2 | 7/2013 | Field |
| 8,579,931 B2 | 11/2013 | Chesbrough et al. |
| 8,626,269 B2 | 1/2014 | Jones et al. |
| 8,626,270 B2 | 1/2014 | Burbank et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0188195 A1 | 12/2002 | Mills |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |

(56) References Cited

U.S. PATENT DOCUMENTS

| | | |
|---|---|---|
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2004/0253185 A1 | 12/2004 | Herweck et al. |
| 2004/0265371 A1 | 12/2004 | Looney et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0276492 A1 | 11/2007 | Andrews et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0091120 A1 | 4/2008 | Fisher |
| 2008/0097199 A1 | 4/2008 | Mullen |
| 2008/0121242 A1 | 5/2008 | Revie et al. |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2010/0030072 A1 | 2/2010 | Casanova et al. |
| 2010/0042041 A1 | 2/2010 | Tune et al. |
| 2010/0298696 A1 | 11/2010 | Field et al. |
| 2011/0184280 A1 | 7/2011 | Jones et al. |
| 2011/0184449 A1 | 7/2011 | Lubock et al. |
| 2012/0078092 A1 | 3/2012 | Jones et al. |
| 2012/0116215 A1 | 5/2012 | Jones et al. |
| 2012/0179251 A1 | 7/2012 | Corbitt, Jr. |
| 2012/0215230 A1 | 8/2012 | Lubock et al. |
| 2013/0144157 A1 | 6/2013 | Jones et al. |
| 2013/0190616 A1 | 7/2013 | Casanova et al. |
| 2013/0253315 A1 | 9/2013 | Burbank et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |
| 2014/0142696 A1 | 5/2014 | Corbitt, Jr. |
| 2014/0243675 A1 | 8/2014 | Burbank et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 | 10/2004 |
| GB | 708148 | 4/1954 |
| JP | 2131757 A | 5/1990 |
| JP | 2006516468 A | 7/2006 |
| JP | 2007537017 A | 12/2007 |
| WO | 8906978 A1 | 8/1989 |
| WO | 9112823 A1 | 9/1991 |
| WO | 9314712 A1 | 8/1993 |

(56) References Cited

FOREIGN PATENT DOCUMENTS

| WO | 9317671 | A1 | 9/1993 |
|---|---|---|---|
| WO | 9317718 | A1 | 9/1993 |
| WO | 9416647 | A1 | 8/1994 |
| WO | 9507057 | A1 | 3/1995 |
| WO | 9806346 | A1 | 2/1998 |
| WO | 9908607 | A1 | 2/1999 |
| WO | 9935966 | A1 | 7/1999 |
| WO | 9951143 | A1 | 10/1999 |
| WO | 0023124 | A1 | 4/2000 |
| WO | 0024332 | A1 | 5/2000 |
| WO | 0028554 | A1 | 5/2000 |
| WO | 0054689 | A1 | 9/2000 |
| WO | 0108578 | A1 | 2/2001 |
| WO | 0170114 | A1 | 9/2001 |
| WO | 0207786 | A2 | 1/2002 |
| WO | 03000308 | A1 | 1/2003 |
| WO | 2004045444 | A2 | 6/2004 |
| WO | 2005013832 | A1 | 2/2005 |
| WO | 2005089664 | A1 | 9/2005 |
| WO | 2005112787 | A2 | 12/2005 |
| WO | 2006012630 | A2 | 2/2006 |
| WO | 2006056739 | A2 | 6/2006 |
| WO | 2006097331 | A2 | 9/2006 |
| WO | 2006105353 | A2 | 10/2006 |
| WO | 2007067255 | A1 | 6/2007 |
| WO | 2007069105 | A2 | 6/2007 |
| WO | 2008077081 | A2 | 6/2008 |

OTHER PUBLICATIONS

Johnson & Johnson: Breast Biopsy (minimally invasive): Surgical Technique: Steps in the MAMOTOME Surgical Procedure. From http://www.jnjgateway.com. 3 pages, 2000.
Johnson & Johnson: New Minimally Invasive Breast Biopsy Device Receives Marketing Clearance in Canada; Aug. 6, 1999. From http://www.jnjgateway.com. 4 pages.
Johnson & Johnson: Mammotome Hand Held Receives FDA Marketing Clearance for Minimally Invasive Breast Biopises; Sep. 1, 1999. From From http://www.jnjgateway.com. 5 pages.
Johnson & Johnson: The Mammotome Breast Biopsy System. From: http://www.breastcareinfo.com/aboutm.htm. 6 pages.
Cook Incorporated: Emoblization and Occlusion. From: www.cookgroup.com 6 pages, 1996.
Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.
Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.
Fucci, V., et al., "Large Bowel Transit Times Using Radioopaque Markers in Normal Cats", J. of Am. Animal Hospital Assn., Nov.-Dec. 1995 31 (6) 473-477.
Schindlbeck, N. E., et al., "Measurement of Colon Transit Time", J. of Gastroenterology, No. 28, pp. 399-404, 1990.
Shiga, et al., Preparation of Poly(D, L-lactide) and Copoly(lactide-glycolide) Microspheres of Uniform Size, J. Pharm. Pharmacol. 1996 48:891-895.
Eiselt, P. et al, "Development of Technologies Aiding Large—Tissue Engineering", Biotechnol. Prog., vol. 14, No. 1, pp. 134-140, 1998.
Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.
H. J. Gent, M.D., et al., Stereotaxic Needle Localization and Cytological Diagnosis of Occult Breast Lesions, Annals of Surgery, Nov. 1986, pp. 580-584, vol. 204—No. 5.
Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.
Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.
Collagen—Definitions from Dictionary. com.
Fibrous—Definitions from Dictionary.com.
International Search Report for PCT/US2009/000945 mailed Jul. 16, 2009.
Written Opinion of the International Searching Authority for PCT/US2009/000945 mailed Jul. 16, 2009.
International Search Report for PCT/US2007/016902 mailed Feb. 28, 2008.
International Search Report for PCT/US2007/016902 mailed Feb. 4, 2009.
Written Opinion of the International Searching Authority for PCT/US2007/016902 mailed Feb. 4, 2009.
International Search Report for PCT/US2007016918 mailed Nov. 26, 2007.
Written Opinion of the International Searching Authority for PCT/US2007016918 mailed Feb. 4, 2009.

BIOPSY MARKER WITH IN SITU-GENERATED IMAGING PROPERTIES

PRIORITY DATA AND INCORPORATION BY REFERENCE

This application is a continuation of U.S. patent application Ser. No. 12/519,656 filed Jun. 17, 2009, which is a U.S. national phase of International Application No. PCT/US2007/087768, filed Dec. 17, 2007, which claims priority to U.S. Provisional Patent Application No. 60/870,502, filed Dec. 18, 2006, which are incorporated by reference in their entirety.

TECHNICAL FIELD

The invention relates generally to a biopsy tissue markers. More specifically, the invention further relates to a biocompatible tissue site marker that is visible under various modes of imaging.

BACKGROUND

Advances in modern medical imaging technologies such as X-ray, ultrasound, or magnetic resonance imaging make it possible to identify and to biopsy tumors while they are still small. When dealing with a small tumor, especially after a portion of the tumor has been removed for biopsy, it is sometimes difficult to relocate the tumor at a later time for treatment. This is particularly true in the case of tumors in the breast, where the ability to visualize a small growth may depend upon the manner in which the breast is positioned or compressed during the procedure. In addition, prior to surgically removing a tumor, it is often advantageous to try to shrink the tumor by chemotherapy or irradiation. This is especially true in the case of breast cancer, where conservation of breast tissue is a concern. Shrinkage of the tumor can sometimes make it difficult for the surgeon to locate the tumor.

A solution to this problem is to place a marker within the target tissues at the time of biopsy which can be visualized under a variety of imaging modalities to facilitate finding the tumor at a later time. When a suspicious mass is detected, a sample is taken by biopsy, often, but not necessarily, using a specialized instrument such as a biopsy needle. The needle is inserted in the breast while the position of the needle is monitored using fluoroscopy, ultrasonic imaging, X-rays, MRI or other suitable imaging modalities.

In a new procedure, called stereotactic needle biopsy, the breast is compressed between the plates of a mammography apparatus and two separate X-rays are taken from different points of reference. The exact position of the mass or lesion is calculated within the breast. The coordinates of the lesion are then programmed into a mechanical stereotactic apparatus which guides the biopsy needle to the lesion.

Irrespective of the biopsy technique, the surgical site may need to be examined or accessed for surgical treatment of a cancerous lesion. Treatment requires the surgeon or radiologist locate the lesion precisely and this may need to be done repeatedly over a period of time. Since treatment may alter the host tissue, the function of a marker even more important.

U.S. Pat. No. 6,725,083 for "Tissue site markers for in vivo imaging" describes biopsy site markers and methods that permit conventional imaging techniques to be used, such as ultrasonic imaging. The biopsy site markers have high ultrasound reflectivity due to high contrast of acoustic impedance resulting from gas-filled internal pores. The markers may have a non-uniform surface. The patent discloses the use of materials such as metal, ceramic materials, metal oxides, polymer, and composites and mixtures thereof.

U.S. Pat. No. 6,350,244 for "Bioabsorable markers for use in biopsy procedure" discloses a breast tissue marker that allows the marker to be left in place avoiding the need for surgical removal. One type of marker takes the form of hollow spheres made of polylactite acid filled with iodine or other radiopaque material to make them visible under X-rays and/or ultrasound. The radiopaque materials are also bioabsorbable. Another type of marker disclosed is a solid marker of pre-mixed radiopaque material and a bioabsorbable material. The solid markers may also include dyes and radioactive materials.

U.S. Pat. No. 6,347,241 for "Ultrasonic and x-ray detectable biopsy site marker and apparatus for applying it" shows a biopsy site marker of small bodies or pellets of gelatin which enclose substantially a radioopaque object. The pellets are deposited at the biopsy site by an applicator device inserted in the biopsy site. Several gelatin pellets are deposited through the tube. The radio opaque core in the gelatin bodies are of a non-biological material and structure which are readily identified during X-ray observations.

U.S. Pat. No. 6,161,034 for "Methods and chemical preparations for time-limited marking of biopsy sites" describes markers that remain present to permit detection and location of the biopsy site. The markers are later absorbed by the host. The patent discloses gelatin, collagen, balloons and detectability provided by AgCl; AgI; $BaCO_3$; $BaSO_4$; K; $CaCO_3$; ZnO; $Al_2O_3$; and combinations of these.

US Patent Publication No. 2006/0079805 for "Site marker visible under multiple modalities" describes site markers that include balls or particles which are bonded together to form a marker body. The balls or particles are made from biocompatible materials such as titanium, stainless steel or platinum. The balls or particles are described as being bonded together by sintering or by adhesive such as epoxy. An alternative embodiment has at least one continuous strand of wire of biocompatible material such as titanium, stainless steel, platinum, or other suitable material, compressed to form a mass that resembles a ball of yarn. Another alternative is a resonating capsule, or a rod with drilled holes.

US Patent Publication No. 2006/0036165 for "Tissue site markers for in vivo imaging" shows ultrasound-detectable markers whose shapes are distinct in an image from biological shapes. Various shapes are disclosed including cylinders, coils, and other more complex shapes.

US Patent Publication No. 2005/0234336 for "Apparatus and method for marking tissue" describes permanent biopsy markers that support visualization under multiple modalities such as MRI, X-ray and ultrasound. The marker has a body made of a resilient, preferably non-absorbable polymer material that is radiopaque and echogenic. The material expands in situ. The materials for the marker include polyacrylates, ethylene-vinyl acetates (and other acyl-substituted cellulose acetates), polyurethanes, polystyrenes, polyvinyl oxides, polyvinyl fluorides, poly(vinyl imidazoles), chlorosulphonated polyolefins, polyethylene oxides, polyvinyl alcohols (PVA), polytetrafluoroethylenes and nylons, with the preferred material being polyvinyl alcohol (PVA) and alkylated or acylated derivatives thereof.

U.S. Pat. No. 5,676,146 shows an implant used to repair skeletal defects and irregularities. The implant is of radiolucent material and with a resorbable radiopaque marker, such as nondemineralized or partially demineralized bone particles. A radiopaque component, which is resorbable in its entirety, is included. Examples of materials include demineralized.

alized bone sheet, particles, etc., collagen and collagen derivatives, plastic such as polyethylene cetabular cups.

Collagen has been proposed as a material for implants and various methods of preparation and types of materials are known. Examples are disclosed in U.S. Pat. Nos. 5,800,541; 5,162,430; 5,328,955; and 5,475,052

It is believed that most known tissue markers have a disadvantage in that they are not visible under all available imaging modalities. The features of a marker that make it stand out under X-rays do not necessarily make them stand out under MRI or ultrasound imaging. One prior art mechanism for addressing the need for multiple-imaging-mode markers is to employ a combination of metal structure and biodegradable foam to provide ultrasonic imaging visibility, MRI visibility and x-ray visibility. In this case, the metal structure provides x-ray visibility and biodegradable foam provides visibility in ultrasonic imaging.

There is a need for site markers made from biocompatible materials that are visible under various modes of imaging to reduce the number of procedures that patients must undergo in detection and treatment of cancer or any disease requiring the user of tissue markers. It will be a valuable contribution to the art for a marker with a simple design and superior biocompatibility can be provided.

SUMMARY OF THE INVENTION

A biopsy marker, preferably a breast biopsy marker, has radio-opaque properties that are derived in situ, preferably based on a natural a biological response, such as calcification or accumulation or tissue-concentration of a chemical agent that acts as an imaging contrast. In an embodiment, a biodegradable foam such as collagen foam or gelatin foam is embedded with a biological tissue that is susceptible to the calcification. The biopsy marker is implanted to mark the biopsy site. The foam material provides ultrasonic visibility to access the implantation site. The biological tissue undergoes calcification in 30 days to 5 years depending on the chemistry of biological tissue used. The calcification generated in the biological tissue provides visibility in magnetic resonance imaging (MRI) and X-ray imaging. As a result, the marker may be located using radiation-based imaging or ultrasonic imaging.

Many types of implantable tissues can be used to prepare a biopsy marker described in this invention. The implantable tissues used include but not limited to: bovine pericardium tissue, porcine dermal tissue, bovine or porcine arterial tissue, porcine aortic wall tissue and the like. A tissue that is rich in elastin such as porcine aortic wall tissue is even more preferred. It is believed that elastin rich tissue is highly susceptible to calcification. Biomaterials that are derived from elastin protein may also be used. The biological tissue is preferred to be crosslinked or stabilized using glutaraldehyde. The tissue crosslinked using 0.2 to 2% glutaraldehyde is even more preferred. In addition, biological ingredients that promote calcification may also be added in the tissue. These additives include bioactive and non-bioactive substances like bone growth factor, phospholipids, polyethylene glycol and the like.

In another embodiment, an elastic protein-based biomaterial is processed to cause the material to have a 60 to 90% porosity. The material is further processed to cause crosslinking using glutaraldehyde, 1-Ethyl-3-[3-dimethylaminopropyl]carbodiimide hydrochloride (EDC) or other suitable crosslinker. The elastin foam is then implanted as a biopsy marker where it undergoes rapid calcification. The calcification is then detected using standard X-ray or MRI imaging techniques.

According to an embodiment, an intracorporeal marker marks a site within living tissue of a host. The marker has a body having a first portion of porous biodegradable material having gas-filled voids and at least one second portion including biological material that tends to become calcified in a human host over time. Preferably, the biological material includes a material with elastin as a substantial component. More preferably, the biological tissue includes porcine aortic wall tissue. Even more preferably, the biological tissue includes a material with elastin that has been cross-linked. In any of these embodiments, an agent may be incorporated in the biological material that promotes bone growth. The calcification may be enhanced by use of a bone growth factor, phospholipids, or polyethylene glycol.

In another embodiment, the first portion defines a cylindrical shape and the second portion is encased within it. The biological material may be entirely encased with the body. Preferably, the body (first portion) has gas-filled pores. In an embodiment the first portion includes collagen and/or gelatin.

According to an embodiment, an intracorporeal marker marks a site within living tissue of a host. The marker has a body having a first portion of porous biodegradable material having gas-filled voids and at least one second portion including biological material that tends to become imageable in a human host over time due to a physiological mechanism of the host. Preferably, the biological material includes a material with elastin as a substantial component. More preferably, the biological tissue includes porcine aortic wall tissue. Even more preferably, the biological tissue includes a material with elastin that has been cross-linked. In any of these embodiments, an agent may be incorporated in the biological material that promotes bone growth. The calcification may be enhanced by use of a bone growth factor, phospholipids, or polyethylene glycol.

In another embodiment, the first portion defines a cylindrical shape and the second portion is encased within it. The biological material may be entirely encased with the body. Preferably, the body (first portion) has gas-filled pores. In an embodiment the first portion includes collagen and/or gelatin. In another embodiment, the biological material is capable of interacting with an antibody carrying a chemical substance that can be detected by an imaging modality.

According to another embodiment, a method of in vivo identification of a position in soft tissue, includes: inserting a marker having a first portion that can be imaged with ultrasound and a second portion that promotes calcification; imaging under ultrasound at a first time and imaging under radiation at a second time following the first. The second time preferably follows the first by an interval during which calcification of the second portion occurs. The method may include waiting for the second portion to calcify. The method may include the step of making the marker which may further include using an agent in the marker that promotes bone growth.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

A biopsy marker, preferably a breast biopsy marker, has radio-opaque properties that are derived in situ, preferably based on a natural a biological response, such as calcification or accumulation or tissue-concentration of a chemical agent that acts as an imaging contrast. In an embodiment, a biodegradable foam such as collagen foam or gelatin foam is embedded with a biological tissue that is susceptible to the calcification. The biopsy marker is implanted to mark the biopsy site. The foam material provides ultrasonic visibility to access the implantation site. The biological tissue undergoes calcification in 30 days to 5 years depending on the chemistry of biological tissue used. The calcification generated in the biological tissue provides visibility in magnetic resonance imaging (MRI) and X-ray imaging. As a result, the marker may be located using radiation-based imaging or ultrasonic imaging.

Many types of implantable tissues can be used to prepare a biopsy marker described in this invention. The implantable tissues used include but not limited to: bovine pericardium tissue, porcine dermal tissue, bovine or porcine arterial tissue, porcine aortic wall tissue and the like. A tissue that is rich in elastin such as porcine aortic wall tissue is even more preferred. It is believed that elastin rich tissue is highly susceptible to calcification. Biomaterials that are derived from elastin protein may also be used. The biological tissue is preferred to be crosslinked or stabilized using glutaraldehyde. The tissue crosslinked using 0.2 to 2% glutaraldehyde is even more preferred. In addition, biological ingredients that promote calcification may also be added in the tissue. These additives include bioactive and non-bioactive substances like bone growth factor, phospholipids, polyethylene glycol and the like.

In another embodiment, an elastic protein-based biomaterial is processed to cause the material to have a 60 to 90% porosity. The material is further processed to cause crosslinking using glutaraldehyde, 1-Ethyl-3-[3-dimethylaminopropyl]carbodiimide hydrochloride (EDC) or other suitable crosslinker. The elastin foam is then implanted as a biopsy marker where it undergoes rapid calcification. The calcification is then detected using standard X-ray or MRI imaging techniques.

The shape of the marker can depend on the clinical application. In general cylindrical, spherical, disk like shapes are preferred. Irregular shapes may also be used.

Figure 1:
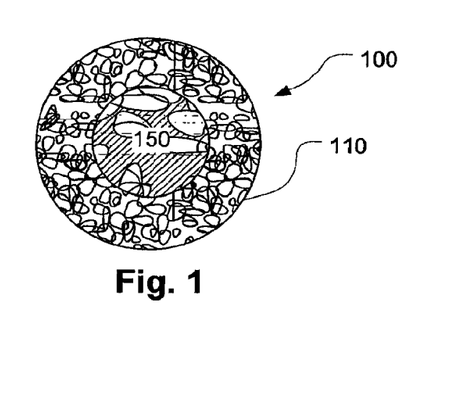
FIG. 1 is a cross-sectional view of a tissue marker of biodegradable foam with biological tissue inside.
Figure 2:
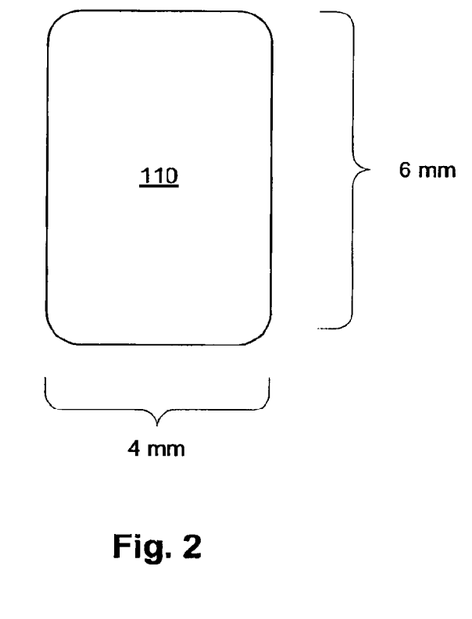
FIG. 2 shows the tissue marker of FIG. 1 from the side.
Figure 3:
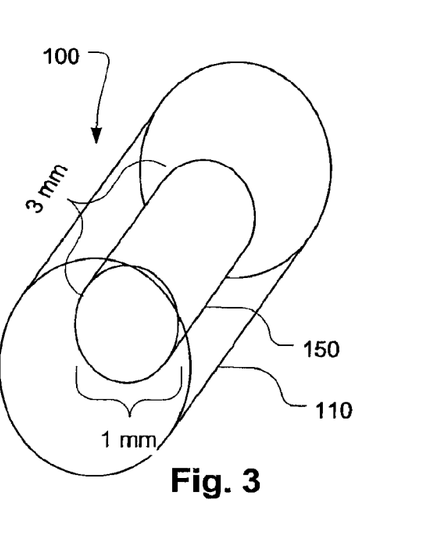
FIG. 3 ghost oblique view of the tissue marker of FIGS. 1 and 2.

Referring now to FIGS. 1-3, a tissue marker 100 has an external layer of biodegradable foam 110 with a core of biological tissue 150. The biodegradable foam has biocompatible gas within its voids. The biocompatible gas provides a low density structure within the marker body which provides high contrast when viewed using ultrasonic imaging equipment. This makes the marker visible under ultrasonic imaging modalities. The biological tissue 150 within is a material chosen for its tendency to calcify when placed in a human host. When the marker is placed within the body of a host, the biodegradable foam is broken down while the biological material 150 calcifies and eventually becomes visible under radiation imaging modalities.

The period during which ultrasound can be used may last between weeks and many months, for example six months. In many therapeutic situations, this is more than sufficient time. The time during which the calcified remainder can be imaged may last for many years or it may be permanent. The calcification may take a year or two to occur. Again, in many therapeutic situations, the radiation-imaging provided in the later stages is all that is required. Therefore the loss of the ability to image under ultrasound is inconsequential.

The benefits of the above device should be apparent. The calcified biological tissue is highly compatible with the host. Some of the bulk of the marker which may be desirable for ultrasound imaging can be lost which may be desirable as well. In a preferred embodiment, which is by no means limiting of the invention, the marker may be generally cylindrical with a diameter of about 4 mm and a length of about 6 mm. The core of biological tissue may be about 1 mm in diameter and about 3 mm long.

Figure 4:
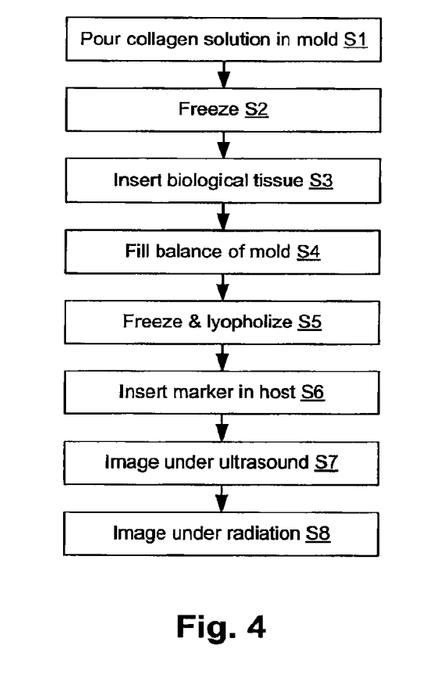
FIG. 4 shows a method of making the tissue marker of FIGS. 1-3 and subsequently using the marker.

One example of a method for making and using the marker is illustrated in FIG. 4. In step S1, a collagen solution is poured into a mold to partly fill the mold. Just enough solution to create a spacer for the biological tissue is all that is required. Then, in step S2, the collagen solution frozen in the mold. The biological material is inserted in the mold and collagen solution is poured into the space around it in step S4. Then the whole mold is frozen and the frozen collagen solution lyophilized in step S5 to remove the ice while leaving the collagen matrix behind.

To use the marker, in step S6, the marker is implanted in a host. This step may be done as part of a biopsy procedure, for example. Then, in step S7, the marker is imaged. Step S7 may occur repeatedly over a range of time, perhaps a year, after implantation. In step S8, perhaps over a year after implantation, the marker is imaged using radiation imaging modalities. Steps S7 and S8 may overlap and are not necessarily chronologically-sequential in all instances. Other steps are not necessarily sequential either. For example, steps S3 and S4 could be done simultaneously—the flow chart presents merely one example of the manufacturing and use processes.

Instead of using collagen foam to form voids, it is possible to form voids in a biodegradable material using other means. For example, voids could be molded in or machined into a piece of material Implantation of a biological material can be done in a similar way, but forming a hole in a pre-made body of biodegradable material, inserting the biological material into the hole and subsequently sealing the hole.

Also, instead of molding the foam, it is possible to form the marker by dipping the biological material body 150 into a collagen or other suitable solution and freezing it in repeated steps until a coating of suitable thickness is obtained before lyophilizing the resulting structure.

As discussed above, the biological tissue 150 may include bovine pericardium tissue, porcine dermal tissue, bovine or porcine arterial tissue, porcine aortic wall tissue and the like. As mentioned, a tissue that is rich in elastin such as porcine aortic wall tissue is even more preferred. It is believed that elastin rich tissue is highly susceptible to calcification. Biomaterials that derived from elastin protein may also be used. The biological tissue is preferred to be crosslinked or stabilized using glutaraldehyde. The tissue crosslinked using 0.2 to 2% glutaraldehyde is even more preferred. In addition, biological ingredients that promote calcification may also be added in the tissue. These additives include bioactive and non-bioactive substances like bone growth factor, phospholipids, polyethylene glycol and the like.

While the above marker example of a cylindrical body is a preferred configuration, other shapes and combinations can be used. For example, more than one body of biological tissue could be integrated in the porous biodegradable body. Also, the biological tissue need not be entirely encased within the body of the biodegradable portion. For example, an alternative method of manufacture may be to co-extrude under pressure such that the casing solution and the biological material are plastic but freeze quickly after exiting the extruder. The sublimation of the solute can then be done to the co-extruded billet before or after dividing it into pieces of appropriate length.

Markers having the above-described structures, or any similar structure, may be used according to the following method which may include steps 1 and 2, steps 1 through 3, or steps 1 through 4, according to different embodiments.

Step 1. Insert a marker at a location. The location can be marked at a time and location of biopsy or otherwise positioned in a tissue mass.

Step 2. Identify a location of the marker using a first imaging modality. The modality may be ultrasound-based imaging. This step may include passing a corresponding form of energy through a soft tissue mass of a living host.

Step 3. Wait a period of time for calcification to occur.

Step 4. Identify a location of the marker using a second imaging modality that is different from the first imaging modality in step 2. The second imaging modality may be X-ray-based imaging or MRI. This step may also include passing a corresponding form of energy through a soft tissue mass of a living host.

Note that in the above method, not all steps are essential or necessarily separate. For example, the waiting step may be inherent in step 2 or step 4.

This specification should not be interpreted as implying that any particular element, step or function is an essential element of any of the claims. The scope of the patented subject matter is defined only by the claims and their equivalents.

The calcification process is not the only kind of biological activity that could be exploited by a marker to cause the marker, or a portion thereof, to become imageable. A marker may incorporate any substance capable of concentrating an imageable substance. For example, the marker could incorporate a substance for which antibodies can be produced. In one exemplary approach, a marker may contain a biological tissue such as bovine pericardium tissue. A bovine tissue specific antibody could be made, labeled with a imaging tag and used. Such antibodies may be grown, radioactively labeled, and injected in the host. The marker would then cause the antibody to concentrate in and about the included substance. This in turn would cause the concentration of the radioactive label to be high in the vicinity of the marker. The process is due to the combined action the antibody and the host. The result may cause the marker to be imageable using a radiation detector.

Using isotopes with a conspicuously-high cross-section for externally applied radiation could also be used to make a marker imageable by the same type of process. That is, the marker may incorporate a substance for which an antibody can be grown. The antibody could be grown using the selected isotope. Due to the combined action the antibody and the host, the antibody concentrates at the marker site. Then, the externally applied radiation may be used to image the concentrated isotope. Antibodies could also serve as carriers of certain molecules or radicals that can be imaged using lower energy radiation due either to their absorption or stimulated-emission signatures. Other labeling methods such as fluorescent labeling useful in fluorescent imaging, paramagnetic labeling useful in MRI imaging and the like may also be used.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. An intracorporeal marker for marking a site within living tissue of a host, the intracorporeal marker comprising:
   an outer body portion of biodegradable material;
   an inner body portion located in the outer body portion, the inner body portion configured to include elastin that becomes calcified in the living tissue of the host over time; and
   an agent configured to interact with the elastin to promote calcification of the elastin of the inner body portion in the living tissue of the host, wherein the agent is selected from a group consisting of bone growth factor, phospholipids, and polyethylene glycol.

2. The marker of claim 1, wherein the biological material inner body portion includes porcine aortic wall tissue.

3. The marker of claim 1, wherein the elastin has been cross-linked.

4. The marker of claim 1, wherein the inner body portion is entirely encased within the outer body portion, and the outer body portion is porous.

5. The marker of claim 1, wherein the outer body portion includes collagen.

6. The marker of claim 1, wherein the outer body portion is a porous gelatin.

7. An intracorporeal marker for marking a site within living tissue of a host, the intracorporeal marker comprising:
   an outer body portion of biodegradable material configured to be ultrasound detectable;
   an inner body portion located in the outer body portion, the inner body portion including elastin configured to calcify in the living tissue of the host over a period of time to enhance X-ray or MRI detectability of the inner body portion; and
   an agent configured to interact with the elastin to promote calcification of the elastin of the inner body portion in the living tissue of the host, wherein the agent is selected from a group consisting of bone growth factor, phospholipids, and polyethylene glycol.

8. The marker of claim 6, wherein the outer body portion is configured to be detectable by ultrasound over a first time period and the inner body portion is configured to undergo calcification to be detectable by X-ray or MRI prior to the expiration of the first time period.

9. The marker of claim 7, wherein the inner body portion is entirely encased within the outer body portion, and the outer body portion is porous.

10. The marker of claim 7, wherein the with elastin has been cross-linked.

11. The marker of claim 7, wherein the inner body portion includes porcine aortic wall tissue.

12. The marker of claim 7, wherein the outer body portion includes porous collagen.

13. The marker of claim 7, wherein the outer body portion is a porous gelatin.

14. An intracorporeal marker for marking a site within living tissue of a human host, the intracorporeal marker comprising:
   an outer body portion of biodegradable material;

an inner body portion located within the outer body portion, the inner body portion including elastin configured to calcify in the living tissue of the human host over time; and an additive that interacts with the elastin to promote calcification of the elastin in the living tissue of the human host, wherein the additive is selected from a group consisting of bone growth factor, phospholipids, and polyethylene glycol.

15. The marker of claim 14, wherein the inner body portion is entirely encased within the outer body portion, and the outer body portion is porous.

16. The marker of claim 14, wherein the biodegradable material of the outer body portion of is one of collagen foam or gelatin foam, and the elastin is embedded in the outer body portion.

* * * * *